(12) United States Patent
Soukal

(10) Patent No.: US 6,422,241 B1
(45) Date of Patent: Jul. 23, 2002

(54) MEDICAL DEVICE WITH SELECTIVELY POSITIONABLE CONTROL UNIT

(75) Inventor: Peter Soukal, Schwarzenbruck (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/572,544

(22) Filed: May 15, 2000

(30) Foreign Application Priority Data

May 14, 1999 (DE) .......................................... 199 22 258

(51) Int. Cl.[7] .............................................. A61G 15/00
(52) U.S. Cl. ............................................. 128/845; 5/616
(58) Field of Search ................................. 128/845, 846, 128/869, 870, 653; 347/255, 260; 5/616

(56) References Cited

U.S. PATENT DOCUMENTS

| | | | |
|---|---|---|---|
| 5,008,921 A | | 4/1991 | Kaul et al. |
| 5,080,100 A | * | 1/1992 | Trotel ...................... 128/653.1 |
| 5,446,548 A | * | 8/1995 | Gerig ......................... 356/375 |
| 5,479,941 A | * | 1/1996 | Harner ....................... 128/845 |
| 5,823,192 A | * | 10/1998 | Kalend ....................... 128/845 |

FOREIGN PATENT DOCUMENTS

| | | |
|---|---|---|
| DE | PS 42 24 246 | 8/1993 |
| DE | OS 43 36 131 | 5/1995 |

* cited by examiner

*Primary Examiner*—Michael A. Brown
(74) *Attorney, Agent, or Firm*—Schiff Hardin & Waite

(57) ABSTRACT

A medical device has at least one displaceable components and a selectively positionable operating unit having a control element for directionally controlling the displacement of the displaceable component. An operating unit position detector and changeover unit is connected to the operating unit and detects the orientation of the operating unit relative to the displaceable component and automatically changes the directional function of the control element in dependent on the orientation of the operating unit relative to the displaceable component.

17 Claims, 2 Drawing Sheets

MEDICAL DEVICE WITH SELECTIVELY POSITIONABLE CONTROL UNIT

BACKGROUND OF THE INVENTION

1. Field of the Invention

The present invention relates to a medical device of the type having at least one displaceable component and with a movable operating unit having control means for directionally controlling the displacement of the component.

2. Description of the Prior Art

German PS 42 24 246 discloses a medical device that has an operating handle via which components of a radiographic diagnostics device can be displaced. For example, the patient support plate can be displaced in the desired direction by means of operating a first switch provided at the operating handle and by means of pivoting the operating handle in a desired displacement direction. Further, it is known to effect a displacement of a central axis of the X-ray radiator by operating a second switch provided at the operating handle such that it follows the direction of the displacement of the operating handle.

European Application 0 363 507 discloses a movable radiographic diagnostic device that has a control station, with a control panel for adjusting and displaying the pickup parameters for a radiograph that can be displaced on its upper side. The control panel can be oriented parallel to both sides and can be oriented parallel to the back face of the control station.

When an operating unit, as described in European Application 0 363 507 is movably arranged with respect to an displaceable component, there is the problem that, when pivoting to the left, a displacement of the support plate along its longitudinal axis ensues to the left when the operating handle is arranged on the left side. For a support plate in a radiographic diagnostic system with an operating handle according to German PS 42 24 246 this is desired. When the operating unit is arranged on the right side of the support plate, however, a pivoting of the operating handle to the left, namely to the side of the lower end, still leads to a displacement of the support plate along its longitudinal direction of its upper end. The same problem arises when the operating unit is arranged on the side of the lower end, since a displacement of the support plate does not ensue to the left but ensues longitudinally in the opposite direction when the operating handle is pivoted to the left. This is not desired, since the operator must always be aware of the orientation of the operating unit in order to pivot the operating handle such that the support plate, or whatever component is being controlled, is displaced in the desired direction.

The same difficulties exist with respect to a hand-held operating unit for a medical device, as described in German OS 43 36 131. This operating unit merely recognizes which of the two sides of the operating unit that are provided with keys or buttons, is on top and which is on the bottom in order to disconnect the keys that are situated on the bottom. Therefore, a number of keys are divided with respect to two surfaces of the operating device, so that the surface does not become excessively large and confusing. An orientation of the operating unit regarding the device to be displaced cannot be seen and therefore the above described directional controlling cannot be achieved.

SUMMARY OF THE INVENTION

An object of the present invention is to provide a medical device of the type initially described wherein a displacement of a component can be effected independently of the orientation of the operating unit with respect to the component, and wherein the displacement is appropriate for the respective function to be performed by the component.

The object is inventively achieved in an apparatus of the type described above having an arrangement for detecting the orientation of the operating unit with respect to the component, as well as for automatically changing the directional function of the control element of the operating unit dependent on the orientation of the operating unit relative to the component in a medical device with at least one displaceable component and with a movable operating unit with the control element directionally controlling the displacement of the component. Therefore, an automatic changeover of the control element ensues without the operator having to consider the orientation of the operating unit with respect to the component, so that erroneous operations or erroneous displacements of the component are avoided.

The displaceable component can be a support device for an examination subject and/or a diagnosis device and/or treatment device, since an erroneous displacement is especially undesired for this type of component, since it requires time and may impair the staff.

DESCRIPTION OF THE PREFERRED EMBODIMENTS

Figure 1:
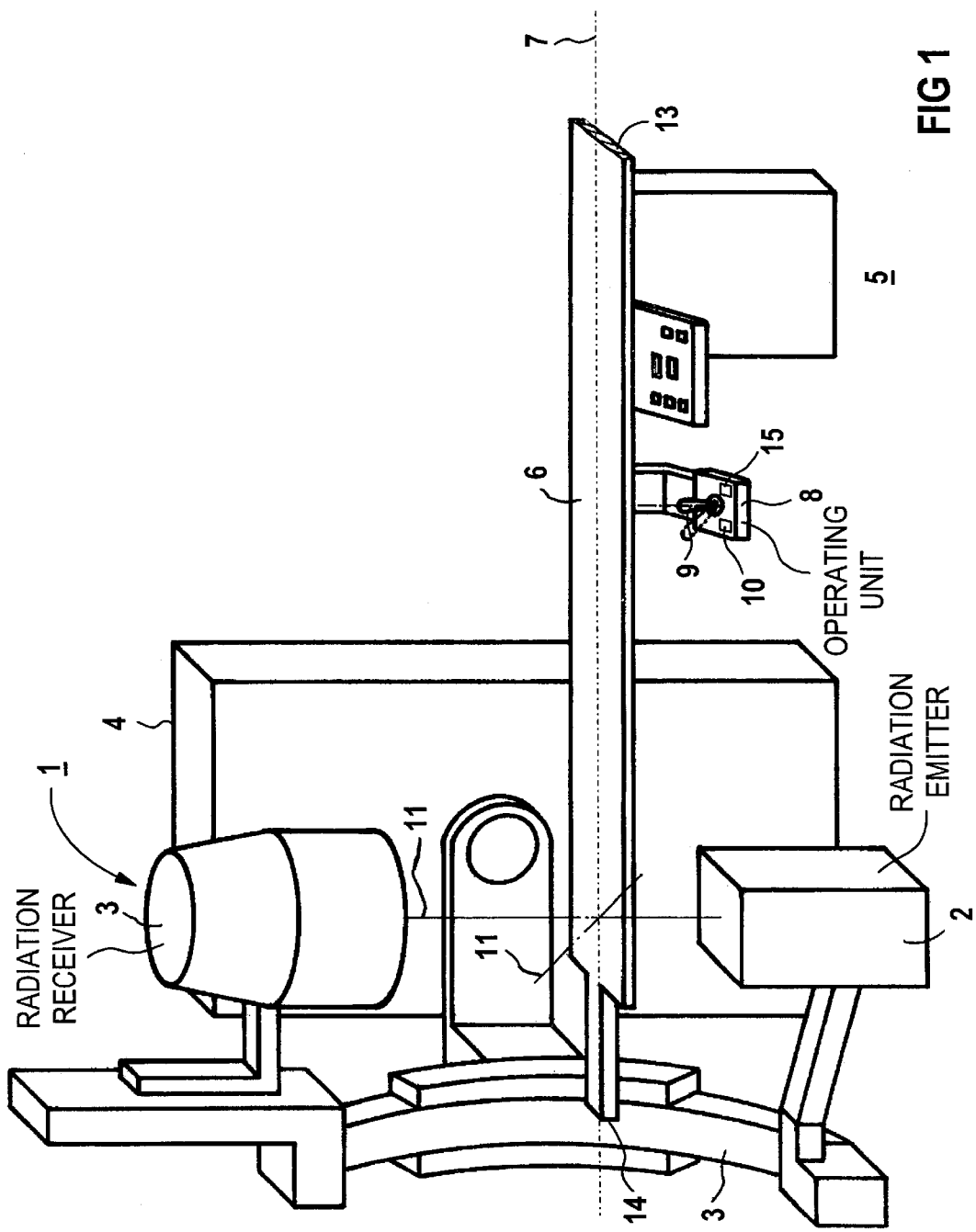
FIG. 1 shows an exemplary embodiment of a medical device according to the invention.

FIG. 1 shows a medical device having a pickup unit 1 composed of aan X-ray transmitter 2 and an X-ray receiver 3 as displaceable component, for example, which can be displaced at a base 4 in the exemplary embodiment. In accordance with the invention, the pickup unit 1 can also be supported at ceiling rails via a stand. Alternatively or in addition, the pickup unit 1 could be fashioned as a therapy unit, as an X-ray therapy unit, for example. In the exemplary embodiment, this medical device further has a support device 5 with a support plate 6 for an examination subject and/or treatment subject, at least the support plate 6 being displaceably borne along its longitudinal axis 7. The displacement possibilities of the support plate 6 are not limited to displacement along the longitudinal axis, it can also be perpendicularly displaced in one direction relative to the longitudinal axis 7 and/or it can be adjusted in height and/or can be pivotable around the longitudinal axis 7, or it can be pivotable around an axis that is perpendicular thereto. For displacing the components of the medical device, electromechanical means, for example, are provided as are known, which can be driven via an operating unit 8. As a control element, the operating unit 8 has a control element, preferably a joystick 9 and associated circuitry with a drive appropriate to the respective function ensuing via the joystick 9. For example, a displacement of the support plate 6 is effected to the left when the joystick 9 is pivoted to the left given the orientation of the operating unit 8 relative to the component, such as the support device 5, particularly the support plate 6, on the left side (shown in FIG. 1). A displacement of the support plate 6 to the right is effected when the joystick 9 is pivoted to the right.

A changeover can ensue via a component changeover key 10, which is provided at the operating unit 8, for example, such either that the support device 5 or the pickup unit 1 can be optionally displaced by means of the joystick 9. Given actuation of the component changeover key 10, a displacement of the pickup unit 1 ensues via the joystick 9, instead of displacement of the support plate 6, such that a central axis 11 of the pickup unit 1 is guided by pivoting the joystick 9, which drives the electro-mechanical means of the pickup unit 1. Pivoted positions of the joystick 9 and the central axis 11 are shown in dotted lines.

Figure 2:
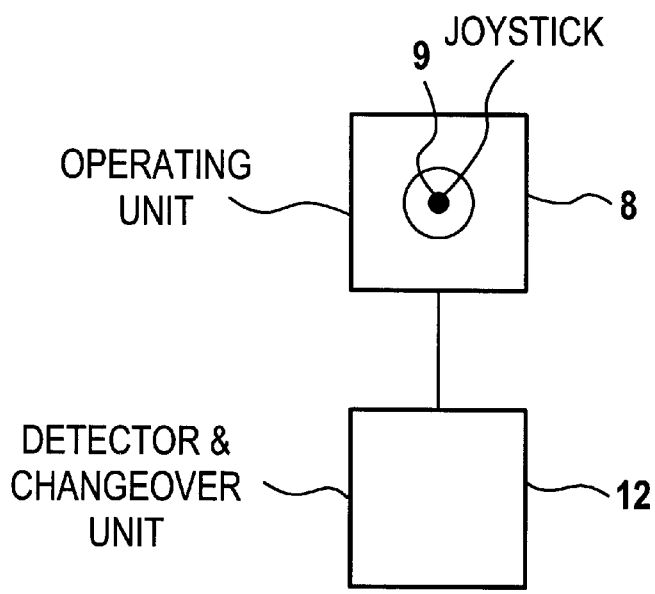
FIG. 2 shows an operating unit and arrangement for detecting the orientation of the operating unit with respect to the component according to FIG. 1.

As shown in FIG. 2, an operating unit location detector and changeover unit 12 is connected to the operating unit 18, for detecting the arrangement of the operating unit 8 with respect to the components 1 and 5 and for automatically changing the directional function of the control element (joystick 9) in dependency on the orientation of the operating unit 8 relative to the components 1 and 5. The directional function of the control element circuitry is changed by the unit 12 dependent on the orientation of the operating unit 8 relative to the components 1 and 5. For example, when the operating unit 8 is arranged on the right side, namely on the opposite side of the support device 5 (compared to the arrangement shown in FIG. 1), the control element is changed such that a displacement of the support plate 6, for example, also ensues to the right, i.e. it ensues in the direction of the head end 14, when the joystick 9 is pivoted to the right. When the joystick 9 is pivoted to the left, a displacement ensues in the opposite direction. Therefore, the control maneuver is in accordance with the respective function. According to a further example, the control element circuitry is switched with respect to placement of the operating unit 8 at the foot end 13 of the support plate 6, such that the support plate 6 is displaced in the direction of the face end 13 when the joystick 9 is pivoted in the direction of the face end 14 of the support plate 6 and when the joystick 9 is pivoted in the opposite direction, a displacement of the support plate 6 ensues in the opposite direction. Such a switching of the control element in accordance with the respective function also ensues when the operating unit 8 is arranged at the face end 14 of the support plate 6. Analogously thereto, given an operation of the component changeover key 10, a displacement of the central axis 11 in accordance with the respective function ensues corresponding to a pivoting of the joystick 9. This can ensue independently of the orientation of the operating unit 8 with respect to the pickup unit 1, according to the invention.

In the framework of the invention, a changeover key 15 can be provided at the operating unit 8, allowing a manual changeover of the control element to be effected by actuating the changeover key 15, so that the operator can intentionally effect a specific control orientation. Taking the shown arrangement of the operating unit 8 at the left side as a basis, a changeover, which is not in accordance with function, of the control element can be effected corresponding to an arrangement of the operating unit 8 at the right side of the support plate 6 or at the foot end 13 or the head end 14.

Figure 3:
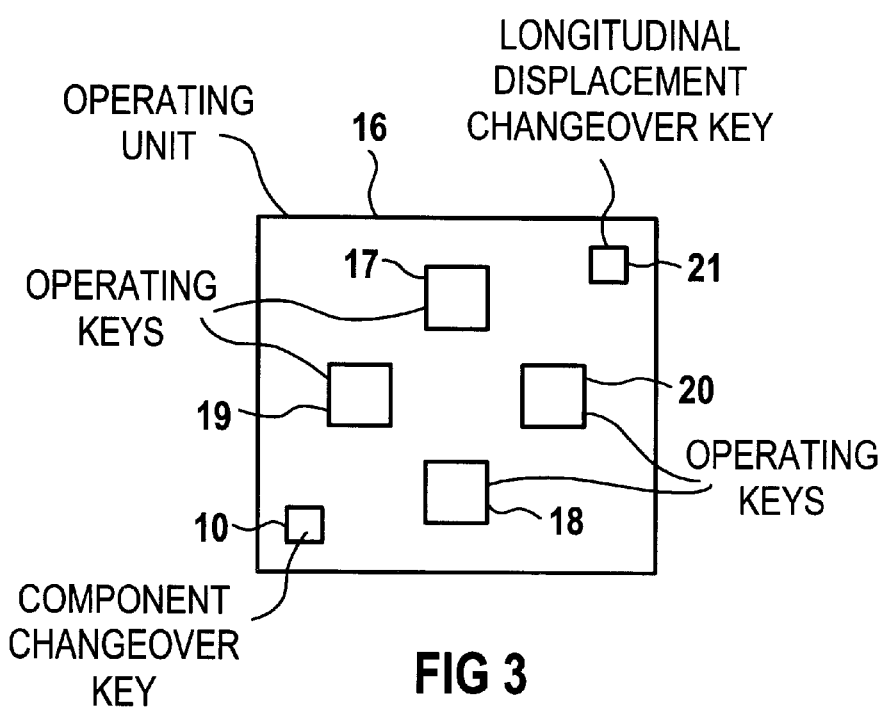
FIG. 3 shows a further exemplary embodiment of an operating unit according to FIGS. 1 and 2.

As an exemplary embodiment, FIG. 3 shows an alternative operating unit 16 having keys 17, 18, 19, 20 for controlling the components 1 and 5. If the alternative operating unit 16 is arranged as shown for the operating unit 8 in FIG. 1, actuation of the key 19, for example, would effect a displacement of the support plate 6 to the left toward the head end 14, and actuation of the Key 20 would effect a displacement of the support plate 6 in the opposite direction. A displacement of the pickup unit 1 can also ensue by using the alternative operating unit 16 by actuation of the component changeover key 10, this displacement being in accordance with the respective functions of the pickup unit.

In accordance with the invention, a displacement of the base 4 and therefore of the pickup unit 1 along the support plate 6 could also be effected via the operating unit 8 or 16 by providing a corresponding longitudinal-displacement key 21 (FIG. 3) via the keys 17, 18, 19, 20 or via the joystick 9. The previously mentioned displacement possibilities of the components 1 and 5 only represent examples in order to explain the principle of the invention. Other displacements of the components 1 and 5 can be effected as well.

In particular, an electronic compass, which detects the orientation of the operating unit 8 or 16 with respect to the components 1 and 5 on the basis of the terrestrial magnetic field, has proven to be advantageous for detecting the arrangement or the orientation of the operating unit 8 or 16 relative to the components 1 and 5. Alternatively, acoustic-, optical-, electromagnetic- or electrostatic reception/transmission means, which cooperate with corresponding reception/transmission means of the operating unit 8 or 16 in order to effect a changeover of the control element in accordance with the respective functions can be provided, for example, at the sides of the components 1 and 5. Transmitters can be provided, for example, on each side of the support device 5, which transmitters emit respectively different signals that are received by a receiver at the operating unit 8 or 16 and on the basis of which a changeover of the control element ensues in accordance with the respective functions. A further alternative is that the unit 12 includes a GPS transmission means or reception means in order to determine the orientation of the operating unit 8 or 16 relative to the components 1 and 5 and to correspondingly change the control element.

In accordance with the invention, the medical device can be a device other a radiographic diagnostics device, for example, an ultrasonic device, magnetic resonance device, computed tomography device, and/or another diagnosis device and/or therapy device. Further, instead of a joystick 9 or a key field (17, 18, 19, 20), a control panel (touch screen) or a force transducer-operating lever can be used for controlling the displacement of the components 1 and 5.

Although modifications and changes may be suggested by those skilled in the art, it is the intention of the inventor to embody within the patent warranted hereon all changes and modifications as reasonably and properly come within the scope of his contribution to the art.

I claim as my invention:

1. A medical device comprising:

a patient support device having a displaceable patient support plate having a head end and a foot end, and a left side and a right side proceeding longitudinally between said head end and said foot end;

a manually actuatable operating unit for controlling displacement of said support plate in different directions, dependent on respective manual actuation actions performed on said operating unit according to a directional function of said operating unit, which sets a relationship between said actuation actions and said different directions said operating unit being selectively positionable at different positions relative to said support plate, said operating unit being positionable at any one of said head end, said foot end, said left side and said right side of said support plate;

a detector and changeover unit connection to said operating unit for detecting a position of said operating unit relative to said support plate and for changing said directional function of said operating unit dependent on the detected position of said operating unit; and said operating unit having manually actuatable first, second, third and fourth actuation elements with which said actuation actions are performed as respective actuations of said first, second, third and fourth actuation elements, and said detector and changeover unit switches said directional function, when said operating unit is detected at said left side, so that actuation of said first actuation element longitudinally displaces said support plate toward said head end and so that actuation of said second actuation element longitudinally displaces said support plate toward said foot end, and said detector and changeover unit switching said directional function, when said operating unit is detected at said right side, so that actuation of said first actuation element longitudinally displaces said support plate toward said foot end and so that actuation of said second actuation element longitudinally displaces said support plate toward said head end, and said detector and changeover unit switching said directional function, when said operating unit is detected at said foot end, so that actuation of said third actuation element longitudinally displaces said support plate toward said head end and so that actuation off said fourth actuation element longitudinally displaces said support plate toward said foot end, and said detector and changeover unit switching said directional function, when said operating unit is detected at said head end, so that actuation of said third actuation element longitudinal displaces said support plate toward said foot end and so that actuation of said fourth actuation element longitudinally displaces said support plate toward said head end.

2. A medical device as claimed in claim 1 wherein said at least one displaceable component comprises a medical diagnostic device.

3. A medical device as claimed in claim 1 wherein said at least one displaceable component comprises a medical treatment device.

4. A medical device as claimed in claim 1 comprising two displaceable components, a first of said displaceable components comprising a patient support plate of a patient support device, and a second of said displaceable components being selected from the group consisting of medical diagnostic devices and medical treatment devices.

5. A medical device as claimed in claim 1 wherein said detector and changeover unit comprises an electronic compass which detects an orientation of said operating unit relative to the earth's magnetic field and supplies a switching signal to said operating unit to switch said directional function of said operating unit dependent on the orientation of the operating unit in the earth's magnetic field.

6. A medical device as claimed in claim 1 wherein said detector and changeover unit comprises a transmission/reception arrangement selected from the group consisting of optical transmission/reception arrangements, acoustic transmission/reception arrangements, electromagnetic transmission/reception arrangements and electrostatic transmission reception arrangements, said transmission/reception arrangement including at least one transmitter and at least one receiver, and said detector and changeover unit supplying a signal to said operating unit to switch said directional function dependent on an orientation of said at least one transmitter relative to said at least one receiver.

7. A medical device as claimed in claim 1 wherein said detector and changeover unit comprises a GPS transmission/reception arrangement and supplies a signal to said operating unit to switch said directional function dependent on an orientation of said operating unit detected by said GPS transmission/reception arrangement.

8. A medical device as claimed in claim 1 wherein said operating unit has a displaceable joystick with which said actuation actions are performed as displacements of said joystick, and wherein displacement of said joystick in respectively different directions causes displacement of said at least one displaceable component in a same direction.

9. A medical device as claimed in claim 1 wherein said operating unit has a key field comprising a plurality of manually actuatable keys with which said actuation actions are performed and which, when actuated, respectively cause displacement of said at least one displaceable component in a direction dependent on said directional function.

10. A medical device comprising:

two displaceable components, a first of said displaceable components comprising a patient support plate of a patient support device, and a second of said displaceable components being selected from the group consisting of medical diagnostic devices and medical treatment devices;

a manually actuatable operating unit for selectively controlling displacement of said first and second displaceable components, one at a time, in different directions, dependent on respective manual actuation actions performed on said operating unit according to a directional function of said operating unit, which sets a relationship between said actuation actions and said different directions, said operating unit being selectively positionable at different positions relative to each of said first and second displaceable components, and said operating unit having a changeover key which, depending on actuation thereof, causes said operating unit to selectively operate either said first displaceable component or said second displaceable component; and a detector and changeover unit connected to said operating unit for detecting a position of said operating unit relative to the displaceable component operable by said operating unit dependent on actuation of said changeover key, and for changing said directional function of said operating unit dependent on the detected position of said operating unit.

11. A medical device as claimed in claim 10 wherein said operating unit has one manually actuatable arrangement used for controlling both said first displaceable component and said second displaceable component.

12. A medical device as claimed in claim 10 wherein said operating unit comprises a first manually actuatable arrangement for controlling said first displaceable component and a second manually actuatable arrangement for controlling said second displaceable component, dependent on actuation of said changeover key.

13. A medical device as claimed in claim 10 wherein said detector and changeover unit comprises an electronic compass which detects an orientation of said operating unit relative to the earth's magnetic field and supplies a switching signal to said operating unit to switch said directional function of said operating unit dependent on the orientation of the operating unit in the earth's magnetic field.

14. A medical device as claimed in claim 10 wherein said detector and changeover unit comprises a transmission/reception arrangement selected from the group consisting of optical transmission/reception arrangements, acoustic transmission/reception arrangements, electromagnetic transmission/reception arrangements and electrostatic transmission reception arrangements, said transmission/reception arrangement including at least one transmitter and at least one receiver, and said detector and changeover unit supplying a signal to said operating unit to switch said directional function dependent on an orientation of said at least one transmitter relative to said at least one receiver.

15. A medical device as claimed in claim 10 wherein said detector and changeover unit comprises a GPS transmission/reception arrangement and supplies a signal to said operating unit to switch said directional function dependent on an orientation of said operating unit detected by said GPS transmission/reception arrangement.

16. A medical device comprising:

at least one displaceable component;

a manually actuatable operating unit having a joy stick for controlling displacement of said component in different directions, dependent on respective manual actuation actions performed on said joy stick according to a directional function of said operating unit, which sets a relationship between said actuation actions and said different functions, said operating unit being selectively positionable at different positions relative to said component; and a detector and changeover unit connected to said operating unit for detecting a position of said operating unit relative to said component and for changing said directional function of said operating unit dependent on the detected position of said operating unit so that displacement of said joy stick in respectively different directions always causes displacement of said at least one displaceable component in a same direction.

17. A medical device comprising:

at least one displaceable component;

a manually actuatable operating unit, having a key field with a plurality of manually actuatable directionally designated keys, for controlling displacement of said component in different directions, dependent on actuation of respective keys of said key field, according to a directional function of said operating unit, which sets a relationship between said actuation actions and said different directions, said operating unit being selectively positionable at different positions relative to said component; and a detector and changeover unit connected to said operating unit for detecting a position of said operating unit relative to said component and for changing said directional function of said operating unit dependent on the detected position of said operating unit, so that respective actuation of said keys always caused displacement of said at least one displaceable component in the respective directions designated by the respective keys.

* * * * *